(12) United States Patent
Alvey et al.

(10) Patent No.: US 9,375,028 B2
(45) Date of Patent: Jun. 28, 2016

(54) COMPOSITIONS AND METHODS FOR NUTRIENT DELIVERY

(75) Inventors: John D. Alvey, Evansville, IN (US); Carol Lynn Berseth, Evansville, IN (US); Deborah Schade, Evansville, IN (US); Kristin Morris, Evansville, IN (US)

(73) Assignee: Mead Johnson Nutrition Company, Glenview, IL (US)

( * ) Notice: Subject to any disclaimer, the term of this patent is extended or adjusted under 35 U.S.C. 154(b) by 498 days.

(21) Appl. No.: 12/963,762

(22) Filed: Dec. 9, 2010

(65) Prior Publication Data
US 2012/0149774 A1 Jun. 14, 2012

(51) Int. Cl.
*A61K 31/20* (2006.01)
*A23L 1/29* (2006.01)
*A23L 1/30* (2006.01)

(52) U.S. Cl.
CPC ............... *A23L 1/296* (2013.01); *A23L 1/3006* (2013.01); *A23V 2002/00* (2013.01)

(58) Field of Classification Search
CPC ................... A23V 2002/00; A23V 2200/322; A23V 2250/1862; A23V 2250/1868; A23L 1/296; A23L 1/3006
See application file for complete search history.

(56) References Cited

U.S. PATENT DOCUMENTS

| | | | |
|---|---|---|---|
| 5,658,767 A | 8/1997 | Kyle | |
| 6,036,992 A | 3/2000 | Borror et al. | |
| 6,753,350 B1 | 6/2004 | Hansen et al. | |
| 8,137,718 B2 | 3/2012 | Russell et al. | |
| 2006/0147579 A1* | 7/2006 | Hamre | 426/2 |
| 2006/0286205 A1* | 12/2006 | Fichtali et al. | 426/7 |
| 2008/0057178 A1* | 3/2008 | Rueda et al. | 426/656 |
| 2010/0267830 A1 | 10/2010 | Gibson et al. | |
| 2011/0208153 A1 | 8/2011 | Alvey | |

FOREIGN PATENT DOCUMENTS

| | | |
|---|---|---|
| CN | 101259101 | 9/2008 |
| CN | 102696761 | 10/2012 |
| WO | 2004112507 | 12/2004 |
| WO | 20070039596 | 4/2007 |
| WO | WO2010033775 | 3/2010 |
| WO | 2010134800 | 11/2010 |

OTHER PUBLICATIONS

Simoens et al., "Inclusion of 10% fish oil in mixed medium-chain triacylglycerol-long-chain triacylglycerol emulsions increase plasma triacylglycerol clearance and induces rapid eicospentaenoic acid (20:5n-3) incorporation into blood cell phospholipids," Am. J. Clin. Nutri., 2008; 8: pp. 282-288.*

Derwent Abstract for CN 101259101A. Original Publication Date: Sep. 10, 2008. Accession Date: Mar. 8, 2015.*

Gruger et al., "Fatty Acid Composition of Oils from 21 Species of Marine Fish, Freshwater Fish and Shellfish," Journal of the American Oil Chemists Society, Oct. 1964, vol. 41, Issue 10, pp. 662-667.*

Carnielli, V., et al., The very low birth weight premature infant is capable of synthesizing arachidonic acid and docosahexaenoic acids from linoleic and linolenic acids. Pediatric Research. 1996;40:169-174.

Henriksen, C., et al. Improved cognitive development among preterm infants attributable to early supplementation of human milk with docosahexaenoic acid and arachidonic acid. Pediatrics. 2008;121:1137-1145.

Koletzko, B., et al., Long chain polyunsaturated fatty acids (LC-PUFA) and perinatal development. Acta Paediatr. 2001;90:460-464.

Lee, H.D., et al. The essentiality of arachidonic acid and docosahexaenoic acid. Prostaglandins, Leukotrienes and Essential Fatty Acids. 2009;81:165-170.

Makrides, M., et al. Fatty acid composition of brain, retina, and erythrocytes in breast- and formula-fed infants. Am J Clin Nutr. 1994;60:189-194.

Markrides, M., et al. Neurodevelopmental outcomes of preterm infants fed high-dose docosahexaenoic acid: a randomized controlled trial. J Am Med Assoc. 2009;301:175-182.

Sangiovanni, J.P., et al. Meta-analysis of dietary essential fatty acids and long-chain polyunsaturated fatty acids as they related to visual resolution acuity in healthy preterm infants. Pediatrics. 2000;105:1292-1298.

Skouroliakou, M., et al. Comparison of two types of TPN prescription methods in preterm neonates. Pharm World Sci. 2009;31:202-208.

Smithers, L.G., et al. Effect of long-chain polyunsaturated fatty acid supplementation of preterm infants on disease risk and neurodevelopment: a systemic review of randomized controlled trials. Am J Clin Nutr. 2008;87:912-920.

Smithers, L.G., et al. Higher dose of docosahexaenoic acid in the neonatal period improves visual acuity of preterm infants: results of a randomized controlled trial. Am J Clin Nutr. 2008;88:1049-1056.

Clandinin, M. et al., "Assessment of the Efficacious Dose of Arachidonic Acids in Preterm Infant Formulas: Fatty Acid Composition of Erythrocyte Membrane Lipids," Pediatric Research, vol. 6, No. 42, Dec. 1, 1997, pp. 819-825.

Clandinin, M. et al., "Growth and development of preterm infants fed infant formulas containing docosahexaenoic acid and arachidonic acid," Journal of Pediatrics, vol. 146, No. 4, Apr. 1, 2005, pp. 461-468.

(Continued)

*Primary Examiner* — Sreeni Padmanabhan
*Assistant Examiner* — Jody Karol
(74) *Attorney, Agent, or Firm* — Patterson Intellectual Property Law, P.C.; James R. Cartiglia

(57) ABSTRACT

The present disclosure provides compositions and methods for delivering nutrients to subjects requiring small-volume nutritional support, such as preterm infants. The compositions may comprise an emulsion of docosahexaenoic acid (DHA) and arachidonic acid (ARA). The nutritional compositions are useful, for example, in correcting nutritional deficiencies by increasing a subject's intake of nutrients, such as ω-3 or ω-6 long-chain polyunsaturated acids. The nutritional compositions are suitable for enteral delivery as a nutritional supplement or for oral delivery as a human milk or infant formula fortifier.

15 Claims, No Drawings

(56) References Cited

OTHER PUBLICATIONS

Innis, S., et al., "Docosahexaenoic acid and arachidonic acid enhance growth with no adverse effects in preterm infants fed formula," The Journal of Pediatrics, vol. 140, No. 5, May 2, 2002, pp. 547-554.

Clandinin, M. et al., "Requirements of newborn infants for long chain polyunsaturated fatty acids". Acta Paediatr Scand 1989; 351 Suppl: 63-71.

Davies, D.P., "Adequacy of expressed breast milk for early growth of preterm infants", Archives of Disease in Childhood, 52, p. 296-301, 1997.

Driscoll, D. et al., "Pharmaceutical and clinical aspects of parenteral lipid emulsions in neonatology", Clinical Nutrition (2008) 27, 497-503.

Lapitlonne, A. et. al, "Reevaluation of the DHA requirement for the premature infant", Prostaglandins, Leukotrienes and Essential Fatty Acids 81 (2009) 143-150.

Moodley, T., et al. "Arachidonic and Docosahexaenoic Acid Deficits in Preterm Neonatal Mononuclear Cell Membranes. Implications for the Immune Response at Birth," Nutrition and Health, 2009, vol. 20, pp. 167-185.

Smithers, L.G. et al., "Effect of two doses of docosahexaenoic acid (DHA) in the diet of preterm infants on infant fatty acid status: Results from the DINO trial", Prostaglandins, Leukotrienes and Essential Fatty Acids 79 (2008) 141-146.

Lehner, F., et al., "Metabolic effects of intravenous LCT or MCT/LCT lipid emulsions in preterm infants," Journal of Lipid Research, vol. 47. 2006, pp. 404-411.

\* cited by examiner

COMPOSITIONS AND METHODS FOR NUTRIENT DELIVERY

BACKGROUND OF THE DISCLOSURE

1. Technical Field

The present disclosure relates to improved enteral nutritional compositions comprising docosahexaenoic acid (DHA) and arachidonic acid (ARA) and also to methods for providing nutritional support in the form of a stabilized emulsion to a population of subjects suffering from nutritional deficiencies, such as preterm and/or low-birth-weight infants. The liquid nutritional composition of the present disclosure may contain a lipid component that contains an emulsion of DHA and/or arachidonic acid (ARA) that is dispersed in an aqueous component comprising nutrients such as amino acids, vitamins, minerals and additional nutrients, or combinations of the foregoing. The nutritional composition may be suitable for enteral delivery via nasogastric tube, intragastric feeding, transpyloric administration and/or any other means of administration that results in the introduction of the nutritional composition directly into the digestive tract of a subject. In some embodiments, the nutritional composition is a fortifier suitable for addition to human milk or infant formula for oral feeding.

2. Background Art

The present disclosure relates to an improved enteral nutritional composition that addresses nutritional deficiencies in ill populations as well as physiological and other consequences often arising from those deficiencies. In particular, the disclosure addresses nutritional deficiencies that may arise in preterm and/or low-birth-weight infants.

Nutritional support for a preterm infant is of great importance since short-term survival and long-term growth and development are at stake. Important goals when providing nutritional support to preterm infants include promoting growth rates and nutrient accretion that are equivalent to those achieved during fetal development, thereby optimizing neurodevelopmental outcomes and laying strong foundations for long-term health. These goals are not easily attained, as the critically ill, low-birth-weight, premature infant often cannot tolerate traditional enteral feeding due to concomitant pathologies or immaturity of the intestinal tract and other organ systems. Thus, total parenteral nutrition (TPN) is indicated as either the only or the preferred method of providing nutrition support. And although TPN can be life saving, it is not a perfect means of nutritional support. TPN lacks many critical nutrients, and its limitations may have long-lasting physiological and developmental consequences for infants.

Low-birth-weight and very-low-birth-weight infants are particularly susceptible to both postnatal growth failure and nutrient deficiencies. Yet, TPN fails to provide an adequate supply of valuable nutrients, such as docosahexaenoic acid and/or arachidonic acid. Accordingly, many preterm infants do not receive an adequate supply of DHA and/or ARA.

In healthy subjects consuming a normal diet, wherein the normal diet provides sufficient DHA and ARA, there is generally no need for DHA or ARA supplementation because considerable amounts of both ARA and DHA are deposited in the human brain and other tissues during intrauterine and postnatal growth. (Clandinin M T et al., "Requirements of newborn infants for long chain polyunsaturated fatty acids". Acta Paediatr Scand 1989; 351 Suppl: 63-71.) In fact, the fetus accumulates long chain polyunsaturated fatty acids (LCPUFAs) such as DHA and ARA during the last trimester of pregnancy, as the placenta provides the fetus with DHA and ARA. (A. Lapitlonne et. Al, "Reevaluation of the DHA requirement for the premature infant" Prostaglandins, Leukotrienes and Essential Fatty Acids 81 (2009) 143-150.) But in cases of preterm birth, an infant faces the sudden loss of the placental LCPUFA supply. Premature infants are often critically ill and face numerous physiological stresses that may rapidly exhaust their available LCPUFA stores, and the resulting LCPUFA deficit may increase the more premature the infant.

Meeting the nutritional needs of preterm infants is problematic due to their gastrointestinal immaturity, poor nutrient stores and the high demand for nutrients to support growth. (L. G. Smithers et al., "Effect of two doses of docosahexaenoic acid (DHA) in the diet of preterm infants on infant fatty acid status: Results from the DINO trial", Prostaglandins, Leukotrienes and Essential Fatty Acids 79 (2008) 141-146.) Yet, in critically ill, preterm infants, it appears that an inadequate supply of essential fatty acids and their derivatives may lead to long-term impairments in visual function and in neurodevelopment. (D. Driscoll et al., "Pharmaceutical and clinical aspects of parenteral lipid emulsions in neonatology", Clinical Nutrition (2008) 27, 497-503.) These problems are exacerbated by the absence of long-chain polyunsaturated acids, such as DHA and ARA, in parenteral nutrition and TPN solutions.

Indeed, TPN and other parenteral nutritional supplements that are currently on the market provide, at best, only negligible amounts of preformed DHA and ARA. DHA is an omega-3-fatty acid and is the most abundant long chain polyunsaturated fatty acid in the brain and retina and is thought to be essential for proper brain and vision development of infants. Although a metabolic pathway exists for biosynthesis from dietary linolenic acid, the pathway is bioenergetically unfavorable, and mammals obtain most of their DHA from preformed DHA provided via dietary sources. For infants, then, the source of DHA is typically human milk; however, DHA is typically absent from parenteral formulas provided to preterm infants.

Parenteral formulas also generally fail to provide sufficient amounts of arachidonic acid. ARA is an omega-6 LCPUFA that serves a major role as a structural lipid associated with phospholipids in the blood, liver, muscle and other major organ systems. ARA is synthesized by the elongation and desaturation of linoleic acid. However, most ARA must be provided in the diet. ARA is especially important during periods of rapid body growth, and is, therefore, an important component of infant nutrition.

Numerous studies have indicated that unsupplemented preterm milk provided to infants provides inadequate quantities of several nutrients required to meet the needs of pre-term infants (Davis, D. P., "Adequacy of expressed breast milk for early growth of preterm infants", Archives of Disease in Childhood, 52, p. 296-301, 1997). While exact needs vary among infants due to differences in activity, energy expenditure, efficiency of nutrient absorption, illness and the ability to utilize energy for tissue synthesis, presently available parenteral nutritional sources are inadequate.

Moreover, feeding volume is often not well tolerated in preterm infants, and nutrients must be provided in an acceptable volume, often via enteral administration. An appropriate method of enteral feeding for a preterm infant is based on gestational age, birth weight, clinical condition and on the opinion of presiding medical personnel. Specific feeding decisions are made based on an infant's ability to coordinate sucking, swallowing and breathing. Frequently, preterm infants or infants who are less mature, weak or critically ill require feeding by tube to avoid risks of aspiration and to conserve energy.

Nasogastric feedings are commonly used in neonatal intensive care units and may be accomplished with bolus or continuous infusions of fortified human milk or other nutritional supplements. Continuous feedings may be better tolerated by very low birth weight infants and infants who have not previously tolerated bolus feedings; however, as previously discussed, reduced or deficient nutrient delivery is a problem associated with continuous feeding methods known in the art.

Therefore, there is a need for stable nutritional compositions that are well-tolerated by preterm infants and that can be easily administered to subjects suffering from nutritional deficiencies in forms and manners that are readily accepted by the subject and the caregiver.

Populations, such as preterm infants, often suffer nutritional deficiencies because they are provided with diets lacking critical nutrients as described above. Thus, a need exists in the art to provide a nutritional composition comprising valuable nutrients that support infant development, such as DHA and ARA. Therefore, the nutritional compositions and methods of the present disclosure provide enteral nutritional support to subjects suffering from nutritional deficiencies in order to promote optimum health and development by delivering important nutrients that are either absent from or provided in inadequate amounts in parenteral nutrition and other infant formulas.

SUMMARY OF THE DISCLOSURE

Briefly, therefore, the present disclosure is directed to a stable nutritional composition for addressing nutritional deficiencies in subjects, such as preterm infants, requiring small-volume nutritional support and to methods for promoting healthy development of those subjects. The present disclosure provides compositions for administering fatty acids, such as DHA and/or ARA and other nutrients to a subject in order to prevent development of nutritional deficiencies and/or to correct existing nutritional deficiencies by increasing a subject's intake of nutrients, such as ω-3 or ω-6 long-chain polyunsaturated acids.

In one embodiment, the present disclosure comprises a nutritional composition, comprising an emulsion of docosahexaenoic acid and/or arachidonic acid.

In another embodiment, the present disclosure comprises a method for providing nutritional support to a subject, the method comprising administering to the subject a nutritional composition comprising an emulsion of docosahexaenoic acid and/or arachidonic acid.

Yet another embodiment comprises a nutritional supplement for fortifying human milk or infant formula suitable for oral administration.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION OF THE DISCLOSURE

The present disclosure provides nutritional compositions and methods for providing nutritional support. The nutritional compositions include a lipid component comprising DHA and ARA and are suitable for delivery to subjects suffering from nutritional deficiencies, such as preterm infants. The present disclosure further provides an improved fortifier for addition to human milk, or infant formula. The fortifier comprises a stable emulsion of DHA and ARA. The present disclosure still further provides methods for providing nutritional support to subjects, such as preterm infants. A full and enabling disclosure of the present disclosure, including the best mode thereof directed to one of ordinary skill in the art, is set forth in the specification below.

Hereinafter, "enteral administration" includes, but is not limited to, feeding via nasogastric tube, orogastric feeding, intragastric feeding, or transpyloric administration. "Enteral administration" may also include any other method known in the art for introducing a nutritional composition directly into the digestive tract other than via oral feeding.

The phrase "nutritional composition" includes nutritional supplements, human milk fortifiers, infant formula fortifiers, and the like, but is not limited to the same. The nutritional compositions of the present disclosure may be suitable for either enteral or oral administration.

"Preterm infant" means a subject born before 37 weeks gestational age. The phrase "preterm infant" is used interchangeably with the phrase "premature infant."

"Low birth weight infant" means an infant born weighing less than 2500 grams (approximately 5 lbs, 8 ounces).

"Very low birth weight infant" means an infant born, weighing less than 1500 grams (approximately 3 lbs, 4 ounces).

"Extremely low birth weight infant" means an infant born weighing less than 1000 grams (approximately 2 lbs, 3 ounces).

"infant" means a human subject ranging in age from birth to not more than about one year and includes infants from 0 to about 12 months corrected. The phrase "corrected age" means an infant's chronological age minus the amount of time that the infant was born premature. Therefore, the corrected age is the age of the infant if it had been carried to full term. The term infant includes low birth weight infants, very low birth weight infants, extremely low birth weight infants and preterm infants.

"Emulsion" means a mixture of two or more immiscible liquids comprising a dispersed phase and a continuous phase. In an emulsion, one liquid, called the dispersed phase, is dispersed in the other liquid, called the continuous phase, bulk phase, or aqueous component.

"Unit dose" refers to a single package of a nutritional composition.

All percentages, parts and ratios as used herein are by weight of the total composition, unless otherwise specified.

The nutritional composition of the present disclosure may also be substantially free of any optional or selected ingredients described herein, provided that the remaining nutritional composition still contains all of the required ingredients or features described herein, in this context, and unless otherwise specified, the term "substantially free" means that the selected composition contains less than a functional amount of the optional ingredient, typically less than 0.1% by weight, and also, including zero percent by weight of such optional or selected ingredient.

All references to singular characteristics or limitations of the present disclosure shall include the corresponding plural characteristics or limitations, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the disclosure described herein, as well as any additional or optional ingredients, components or limitations described herein or otherwise useful in nutritional compositions.

As used herein, the term "about" should be construed to refer to both of the numbers specified in any range. Any reference to a range should be considered as providing support for any subset within that range.

The nutritional composition of the present disclosure may provide nutritional support to preterm and/or low-birth-weight infants or to any other patient with unmet nutritional needs. In some embodiments, the nutritional composition is designed to meet specific nutritional needs of individual subjects, such as infants or preterm infants, in stable, unit-dose liquid compositions standardized to a specified caloric content and/or as a concentrate to meet a subject's particular nutritional needs.

Furthermore, the present disclosure provides a nutritional composition that is useful to combat nutritional inadequacy in the provision of nutrients to those subjects relying on partial or total parenteral nutrition, thereby promoting healthy development of a subject. Indeed, the nutritional composition provides effective amounts of nutrients, such as DHA and/or ARA, which will promote, for example, visual, and neural development in an infant.

The present disclosure also provides a method for enterally delivering nutrients to a subject who requires that the nutrients be administered in very small volumes. As used herein, enteral administration includes feeding via nasogastric tube, orogastric feeding, intragastric feeding, transpyloric administration or any other method known in the art for introducing a nutritional composition directly into the digestive tract.

Thus, the present disclosure addresses the needs of any population that may require small volume enteral nutrition support, including but not limited to perisurgical subjects, subject with short-gut syndrome, pediatric intensive care subjects, and/or any population of any age that is unable to fully orally feed or that is receiving minimal enteral nutrition support or TPN.

Specifically, the nutritional composition of the present disclosure may provide infants with beneficial nutrients that are otherwise absent due to a variety of conditions, such as prematurity or trauma. Such nutrients include but are not limited to docosahexaenoic acid, arachidonic acid, and any other water-soluble or lipid-soluble nutrients.

The present disclosure is directed to, in at least one embodiment, a nutritional composition that delivers, in a small volume, a set of specific nutrients to a subject. The resulting nutritional composition may be commercially viable and is practical for use in critical care settings including, but not limited to, the neonatal intensive care unit (NICU), in some embodiments, the nutritional composition of the present disclosure comprises an enteral nutrient delivery system whereby small but precise volumes of nutritional compositions are introduced into the digestive tract of a subject. In some embodiments, the nutritional composition is delivered in a volume dose of at least 0.5 mL. In certain embodiments, the nutritional composition is delivered in a volume dose of between about 0.7 and about 1.3 mL. In certain embodiments, the nutritional composition is delivered in a volume of about 1 mL. In another embodiment, the nutritional composition array be delivered in volumes up to about 1.5 mL or up to about 2 mL.

In some embodiments, the nutritional composition delivers valuable nutrients to a preterm infant or infant in a small-volume liquid dose of about 1 mL. While preterm infants are often too ill to tolerate full enteral feeds, the nutritional compositions of the present disclosure are designed to be administered as a small-volume nutritional supplement that may be directly administered to an infant through, for example, a nasogastric tube that is placed in infants in the NICU. Thus, administration of the presently disclosed nutritional composition may begin on the first day postpartum.

Moreover, the nutritional composition may be administered one or two times daily or more frequently as directed by a medical professional. Indeed, the nutritional composition may be administered three times daily, four times daily or even still more frequently as directed by a medical professional. Administration may begin immediately after birth and may continue as long as a subject is in nutritional need. In some embodiments, the nutritional composition is administered daily to preterm infants until a time equal to full-term gestation. In other embodiments, the nutritional composition is administered to subjects for an amount of time equal to the time that the patient receives full or partial parenteral nutrition.

The nutritional composition of the present disclosure may comprise a nutritional supplement, a human milk fortifier, an infant formula fortifier or any other ingestible nutritional product. Moreover, the disclosed nutritional composition may be provided in any form known in the art, such as a powder, a gel, a suspension, a paste, a solid, a liquid, a liquid concentrate, reconstituteable powdered milk substitute, or a ready-to-use product. In some embodiments, the nutritional composition is a liquid nutritional, supplement suitable for enteral administration. In other embodiments, the nutritional composition is a liquid fortifier that may be easily mixed with human milk or infant formula.

The nutritional composition may comprise a lipid component that contains a fat or a combination of fats in order to deliver a desired blend of fatty acids to a subject. Suitable fat or lipid sources for practicing the present disclosure may be comprise any lipid source known in the art, including but not limited to, animal sources, e.g., milk fat, butter, butter fat, egg yolk lipid; marine sources, such as fish oils, marine oils, single-cell oils; vegetable and plant oils, such as corn oil, canola oil, sunflower oil, soybean oil, palmolein, coconut oil, high oleic sunflower oil, evening primrose oil, rapeseed oil, olive oil, flaxseed (linseed) oil, cottonseed oil, high oleic safflower oil, palm stearin, soy lecithin, palm kernel oil, wheat germ oil, medium chain triglyceride oil.

In some embodiments, the lipid component of the nutritional composition comprises a single fatty acid, such as a long-chain polyunsaturated fatty acid (LCPUFA) or a combination of LCPUFAs. LCPUFAs generally have a carbon chain length of at least 18. Suitable LCPUFAs for inclusion in the nutritional composition include, but are not limited to, $\omega$-3 or $\omega$-6 long-chain polyunsaturated acids, such as arachidonic acid (20:4n-6) and docosahexaenoic acid (22:6n-3). In one embodiment, the lipid component comprises DHA. In other embodiments, the lipid component of the nutritional composition comprises both DHA and ARA. The preferred forms of DHA and ARA incorporated in the nutritional composition are free, non-esterified DHA and ARA.

All or part of the lipid component may comprise a lipid emulsion. In certain embodiments, the lipid component may comprise between about 2.5 and about 5 g per 100 mL of nutritional composition. In some embodiments the nutritional composition may comprise between about 5 and about 20% w/w of the lipid component.

The present disclosure describes compositions and methods for the delivery of lipid emulsions of varying oil composition to preterm infants in order to meet their essential fatty acid requirements and energy needs. The general illness and immature organs of premature infants, together with a reduced endogenous supply of essential fatty acids, necessitates the administration of lipid emulsions very soon after birth. In some embodiments, the present disclosure teaches a non-pharmaceutical nutritional composition comprising LCPUFAs, preferably pre-formed DHA and ARA, delivered in a lipid emulsion. Thus, the nutritional composition addresses unmet nutritional needs and supports optimal growth and development of preterm infants.

The lipid component of the nutritional composition may comprise between about 0.3% and about 5% w/w DHA in some embodiments. In a particular embodiment, the lipid component comprises at least about 0.32% DHA. In other embodiments, the lipid component comprises at least about 0.5% DHA. In some embodiments, the lipid component comprises at least about 1% DHA. In further embodiments, the lipid component comprises at least about 1.5% DHA. It still other embodiments, the lipid component of the nutritional composition comprises at least about 2% DHA. The source of DHA may be any source known in the art, such as, for example, marine oil, fish oil, single cell oil, egg yolk lipid, and brain lipid. The DHA can be in natural or refined form. Further, in one embodiment, the nutritional composition comprises a source of DHA comprising DHASCO® and/or a fungal oil blend.

Likewise, in some embodiments, the nutritional composition may be formulated to deliver at least about 25 mg/kg/day of docosahexaenoic acid to the subject. In some embodiments, the nutritional composition may be formulated to deliver at least about 50 mg/kg/day DHA. In other embodiments, the nutritional composition may deliver at least about 60 mg/kg/day of DHA to the subject. And in some embodiments, the nutritional composition may be formulated to deliver at least about 75 mg/kg/day of docosahexaenoic acid to the subject. In further embodiments, the nutritional composition is formulated to deliver at least about 100 mg/kg/day MIA. Accordingly, then, as many preterm infants weigh between about 500 g and 2000 g, the nutritional composition may be formulated to deliver, for example, between about 12 mg and 200 mg of DHA per day. In some embodiments, the nutritional composition will comprise between about 12 and about 200 mg of DHA per 100 mL.

The lipid component of the nutritional composition may comprise between about 0.5% and about 5% w/w ARA. In one embodiment, the lipid component comprises at least about 0.64% ARA. In other embodiments, the lipid component comprises at least about 0.5% ARA. In some embodiments, the lipid component comprises at least about 1% ARA. In further embodiments, the lipid component comprises at least about 1.5% ARA. It still other embodiments, the lipid component of the nutritional composition comprises at least about 2% ARA. The ARA source may be any source of ARA known in the art. In some embodiments, the nutritional composition comprises a source of ARA comprising ARASCO® and/or a fungal oil blend. In some embodiments, the ARA component of the nutritional supplement comprises about 30% of a fungal oil blend.

The nutritional composition may be formulated to deliver at least about 10 mg/kg/day of arachidonic acid to the subject. In some embodiments, the nutritional composition may be formulated to deliver at least about 15 mg/kg/day of arachidonic acid to the subject. In some embodiments, the nutritional composition may be formulated to deliver at least about 25 mg/kg/day of arachidonic acid to the subject. In some embodiments, the nutritional composition may be formulated to deliver at least about 40 mg/kg/day ARA. In other embodiments, the nutritional composition may deliver at least about 50 mg/kg/day of ARA to the subject. And in some embodiments, the nutritional composition may be formulated to deliver at least about 60 mg/kg/day of ARA to the subject. Accordingly, then, as many preterm infants weigh between about 500 g and 2000 g, the nutritional composition may be formulated to deliver, for example, between about 12 mg and 120 mg of ARA per day.

The nutritional composition may be supplemented with both DHA and ARA as part of the lipid component. In some embodiments, the DHA:ARA ratio is between about 1:6 and 6:1. In other embodiments, the DHA:ARA ratio is between about 1:2 and 2:1. In still further embodiments, the DHA:ARA ratio is about 1:1. In still other embodiments, the DHA:ARA ratio may be from about 3:1 to about 1:9.

In some embodiments, the nutritional composition further comprises a protein component. The protein component may comprise, but is not limited to, milk protein powders, milk protein concentrates, milk protein isolates, nonfat milk solids, nonfat milk, nonfat dry milk, whey protein, whey protein isolates. They protein concentrates, sweet whey, acid whey, casein, acid casein, caseinate (e.g. sodium caseinate, sodium calcium caseinate, calcium caseinate) and any combinations thereof.

In one embodiment, the proteins are provided as intact proteins. In other embodiments, the proteins are provided as a combination of both intact proteins and partially hydrolyzed proteins, with a degree of hydrolysis of between about 4% and 10%. In certain other embodiments, the proteins are more completely hydrolyzed. In yet another embodiment, the protein source may be supplemented with glutamine-containing peptides.

In some embodiments, the nutritional composition comprises a carbohydrate component. The carbohydrates utilized in the nutritional composition may be any digestible carbohydrates, such as dextrose, fructose, sucrose, maltose, maltodextrin, corn syrup solids, or mixtures thereof, depending on usage. Hydrolyzed or partially hydrolyzed proteins and/or carbohydrates may be desirable due to their easy digestibility. Moreover, the nutritional composition may also contain an additional nitrogen source in addition to the identified amino acids and proteins.

The nutritional composition may include a vitamin and mineral component. The vitamin and mineral component may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to the nutritional product in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

The vitamin component of the nutritional composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\gamma$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

In certain embodiments, the nutritional composition of the present disclosure may comprise at least one prebiotic. In this embodiment, any prebiotic known in the art may be added, in a particular embodiment, the prebiotic can be selected from the group consisting of fructo-oligosaccharide, gluco-oligosaccharide, galacto-oligosaccharide, polydextrose, isomalto-oligosaccharide, xylo-oligosaccharide and lactulose.

in certain embodiments of the disclosure, the nutritional composition may contain one or more probiotics. Any probiotic known in the art may be acceptable in this embodiment provided it achieves the intended result. In a particular embodiment, the probiotic may be selected from any *Lactobacillus* species, *Lactobacillus rhamnosus* GG (American Type Culture Collection accession number ATCC 53103), *Bifidobacterium* species, *Bifidobacterium longum*, and *Bifidobacterium animalis* subsp, lactis BB-12 (DSM No. 10140) or combinations thereof.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such new source is now known or later developed.

Many formulas known in the art are prone to physical instability due to syneresis and to the formation of non-dispersible sediments. Instability is caused by the high levels of protein, fats and minerals that known nutritional formulas contain in order to provide adequate nutrition in a reasonable volume. Notably, acidification of traditional enteral formulas may also lead to protein precipitation and phase separation. Precipitated nutrients cannot generally be shaken back into solution, and they do not provide the nutritional benefits required to promote the health of a subject.

However, the nutritional composition of the present disclosure comprises a stable emulsion further comprising an emulsifier. The emulsifier may comprise microencapsulants, surfactants, emulsion stabilizers or a combination thereof. In some embodiments, the emulsifier may comprise, for example, lecithin, mono-glyceride(s) or di-glyceride(s). In some embodiments, the lipid component of the nutritional composition provides fatty acid(s) in the form of a stable emulsion. In other embodiments the nutritional composition may comprise a stabilizer, such as carrageenan, in place of or in addition to an emulsifier.

In some embodiments, the step of emulsifying may be accomplished via mechanical agitation, ultrasonic vibration, heating, or a combination thereof, Emulsification may be accomplished using any method for emulsification known in the art. In one embodiment, emulsification may comprise homogenization. In some embodiments, multiple homogenization steps may be applied to produce the emulsified lipid component of the nutritional composition.

In some embodiments of the stable emulsion, proteins may act as surfactants. Protein surfactants have the capability of spreading at a lipid-water interface in order to reduce droplet coalescence. Indeed, a protein surfactant may lower the interfacial tension between two liquids resulting in the miscibility of the two liquids. The nutritional composition may comprise any emulsifier that is water soluble. The nutritional composition may comprise more than one emulsifier and/or stabilizer in some embodiments.

In one embodiment, the composition comprises an emulsion of at least one LCPUFA that is stabilized by a protein substrate comprising $\alpha$-lactalbumin. The emulsified LCPUFA may comprise DHA. The $\alpha$-lactalbumin acts as a stabilizing agent, specifically as a surfactant. Additional surfactants, emulsion stabilizers and microencapsulants may be utilized in the lipid component but are not required in order to produce the stable emulsion of the nutritional composition of the present disclosure. In some embodiments, the lipid emulsion of the nutritional composition contains oil/lipid droplets ranging from about 0.070 μm to about 1 μm in diameter.

Furthermore, some embodiments of the nutritional composition, such as those that are optimized for preterm infants or critically ill infants, may mimic certain characteristics of human breast milk. Indeed, the nutritional formula may comprise $\alpha$-lactalbumin, which is the dominant whey protein in human breast milk. Adding $\alpha$-lactalbumin to a composition for preterm infants may provide several physiological and nutritional benefits. However, to fulfill the specific DHA requirements of preterm infants, the nutritional composition comprises a higher DHA content than human milk. The enhanced level of DHA of the nutritional composition compensates for any DHA deficit in a preterm infant and/or prevents the appearance of a DHA deficit.

Other nutrients and ingredients, such as amino acids, vitamins, and minerals may be incorporated into the liquid phase, or aqueous element, of the emulsion. It may be advantageous to add such other ingredients directly by mixing into the emulsion after homogenization. Indeed, the stabilized emulsion allows for the incorporation of other nutrients into the aqueous element without desorption, disruption, or coalescence of the lipid droplets.

Moreover, in some embodiments, the nutritional composition comprising the emulsion, is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The present disclosure further provides a method for providing nutritional, support to a subject, such as a preterm infant, that is receiving partial or total parenteral nutrition. The method includes administering to the subject an effective amount of the nutritional composition of the present disclosure. The duration of administration may vary, but the nutritional composition should be administered while the infant is unable to fully feed and/or is receiving full or partial total parenteral nutrition.

The nutritional composition of the present disclosure may be commercially packaged such that it may interface directly with enteral nutrition apparatuses including, but not limited to, nasogastric tubing, percutaneous endoscopic gastronomy, percutaneous endoscopic jejunostomy, transpyloric tubing and the like. Yet, the packaging should be incompatible with intravenous feeding lines in order to minimize the risk of intravenous administration. Such a design is convenient to ensure full delivery of the package contents, to minimize the risk of contamination and to increase compliance. Further, in certain embodiments, the nutritional composition may be packaged in a single unit-dose delivery package of about 1 mL total volume, about 1.5 mL total volume, or about 2 mL total volume. A unit-dose packaging system is preferred in order to minimize dosing errors and reduce risks of contamination.

The nutritional composition may be expelled directly into a subject's intestinal tract. In some embodiments, the nutritional composition is expelled directly into the gut. In some embodiments, the composition may be formulated to be consumed or administered enterally under the supervision of a physician and may be intended for the specific dietary management of a disease or condition for which distinctive nutritional requirements, based on recognized scientific principles, are established by medical evaluation.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

In some embodiments, the nutritional composition may be delivered to an infant from birth until at a time that matches full-term gestation. In some embodiments, the nutritional composition may be delivered to an infant until at least about three months corrected age. In another embodiment, the nutritional composition may be delivered to a subject as long as is necessary to correct nutritional deficiencies. In yet another embodiment, the nutritional composition may be delivered to an infant from birth until at least about one year corrected age.

The nutritional composition of the present disclosure may be standardized to a specific caloric content, it may be provided as a ready-to-use product, or it may be provided in a concentrated form.

The present disclosure provides a nutritional supplement for enteral administration comprising a lipid component that contains an emulsion of at least one fatty acid, wherein the nutritional supplement is designed to correct nutritional deficiencies in a subject, such as a preterm infant, by increasing a subject's intake of nutrients, such as ω-3 or ω-6 long-chain polyunsaturated acids.

In some embodiments, the nutritional composition is a human milk fortifier and/or an infant formula fortifier. In such embodiments, the nutritional composition comprises DHA and ARA in the form of a stabilized emulsion that may be easily mixed with either human milk or infant formula. As an infant transitions from parenteral nutrition support to a combination of oral feeding (infant formula or human milk) in combination with partial parenteral nutrition support, the nutritional composition in the form of a fortifier may be added to the oral feeds in an effort to ensure that adequate levels of DHA and ARA are available to support optimal growth and neurodevelopment in the subject.

The nutritional compositions and methods of the present disclosure provide significant benefits over the prior art by addressing and correcting nutritional deficiencies in currently available products. Further, the nutritional composition of the present disclosure provides valuable nutrients to preterm infants who would not otherwise receive such nutrients when relying on existing sources of TPN.

The following examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the examples, be considered to be exemplary only, with the scope and spirit of the disclosure being indicated by the claims which follow the example.

EXAMPLES

In an embodiment, the nutritional composition of the present disclosure may be formulated to be administered twice daily to an infant weighing about 1 kg. The infant may receive two 1.5 mL servings of the nutritional composition. The nutritional composition may be formulated to deliver about 25.5 mg DHA per day and about 17 mg ARA per day to the infant. An example of the nutritional composition suitable for use in this example is set forth below:

Nutritional Composition 1

| Ingredient | Amount |
| --- | --- |
| DATEM (Diacetyl Tartaric (Acid) Ester of Monoglyceride) | 0.165 grams |
| Citric Acid | 0.40 grams |
| DHASCO | 4.25 grams |
| ARASCO | 2.84 grams |
| Water | 92.0 mL |

Furthermore, in another embodiment, the nutritional composition may be administered to the infant four times per day in an amount of about 1.5 mL per serving. The nutritional composition may be formulated to deliver about 25.5 mg DHA per day and about 17 mg ARA per day to the infant. An example of the nutritional composition suitable for use in this example is set forth below:

Nutritional Composition 2

| Ingredients | Amount |
| --- | --- |
| DATEM (Diacetyl Tartaric (Acid) Ester of Monoglyceride) | 0.083 grams |
| Citric Acid | 0.40 grams |
| DHASCO | 2.12 grams |
| ARASCO | 1.42 grams |
| Water | 92.0 mL |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the preferred versions contained therein.

What is claimed is:

1. A nutritional supplement for enteral administration to preterm infants, consisting of:
    water;
    protein;
    at least one emulsifier;
    a lipid component, wherein the lipid component comprises at least about 0.64% arachidonic acid and at least about 0.32% docosahexaenoic acid, wherein the arachidonic acid and the docosahexaenoic acid are provided in aqueous emulsified form, and
    wherein the supplement is delivered to the infant in a volume dose between about 0.7 mL and 1.3 mL.

2. The nutritional supplement of claim 1, wherein, the lipid component comprises at least about 1% docosahexaenoic acid.

3. The nutritional supplement of claim 1, wherein the lipid component comprises at least about 2% docosahexaenoic acid.

4. The nutritional supplement of claim 1, wherein the nutritional supplement is formulated to deliver at least about 50 mg/kg/day of docosahexaenoic acid.

5. The nutritional supplement of claim 1, wherein the nutritional supplement is formulated to deliver at least about 60 mg/kg/day of docosahexaenoic acid.

6. A nutritional composition for oral administration to preterm infants, consisting of:
    human milk; and
    a volume dose between about 0.7 mL and 1.3 mL of a fortifier consisting of
        water
        at least one emulsifier;
        a lipid component, wherein the lipid component comprises at least about 0.64% arachidonic acid and at least about 0.32% docosahexaenoic acid, wherein the arachidonic acid and the docosahexaenoic acid are provided in aqueous emulsified form.

7. The fortifier of claim 6, wherein the lipid component comprises at least about 1% docosahexaenoic acid.

8. The fortifier of claim 6, wherein the lipid component comprises at least about 2% docosahexaenoic acid.

9. The fortifier of claim 6, wherein the fortifier is formulated to deliver at least about 50 mg/kg/day of docosahexaenoic acid.

10. A method for providing nutritional support to a preterm infant receiving parenteral nutrition, the method comprising:
    enterally administering to the infant a nutritional composition consisting of water, at least one emulsifier; and a lipid component, wherein the lipid component comprises at least about 0.64% arachidonic acid and at least about 0.32% docosahexaenoic acid, wherein the arachidonic acid and the docosahexaenoic acid are provided in emulsified form and wherein the composition is delivered to the infant in a volume dose between about 0.7 mL and 1.3 mL.

11. The method of claim 10, wherein the lipid component comprises at least about 1% docosahexaenoic acid.

12. The method of claim 10, wherein the lipid component comprises at least about 2% docosahexaenoic acid.

13. The method of claim 10, wherein the nutritional composition is administered to the infant in an amount sufficient to deliver at least about 50 mg/kg/day of docosahexaenoic acid.

14. The method of claim 10, wherein the nutritional composition is administered to the infant in an amount sufficient to deliver at least about 60 mg/kg/day of docosahexaenoic acid.

15. The method of claim 10, wherein the nutritional composition is administered to the infant in an amount sufficient to deliver at least about 40 mg/kg/day of arachidonic acid.

\* \* \* \* \*